(12) United States Patent
Forkosh

(10) Patent No.: US 8,011,225 B2
(45) Date of Patent: Sep. 6, 2011

(54) ASSEMBLY FOR MEASURING THE SPECIFIC GRAVITY AND LEVEL OF A LIQUID

(75) Inventor: Dan Forkosh, Atlit (IL)

(73) Assignee: DUCool Ltd., Kibbutz HaHotrim (IL)

( * ) Notice: Subject to any disclaimer, the term of this patent is extended or adjusted under 35 U.S.C. 154(b) by 416 days.

(21) Appl. No.: 12/438,413

(22) PCT Filed: Aug. 24, 2007

(86) PCT No.: PCT/IB2007/004089
§ 371 (c)(1),
(2), (4) Date: Feb. 23, 2009

(87) PCT Pub. No.: WO2008/023282
PCT Pub. Date: Feb. 28, 2008

(65) Prior Publication Data
US 2009/0277264 A1    Nov. 12, 2009

Related U.S. Application Data

(60) Provisional application No. 60/839,872, filed on Aug. 24, 2006.

(51) Int. Cl.
*G01F 23/30* (2006.01)
*G01N 9/00* (2006.01)

(52) U.S. Cl. ......... 73/32 R; 73/447; 73/290 R; 261/128; 62/271

(58) Field of Classification Search .................. None
See application file for complete search history.

(56) References Cited

U.S. PATENT DOCUMENTS

| 576,537 | A | 2/1897 | Barry |
| 1,524,928 | A | 2/1925 | Hardel et al. |
| 3,269,184 | A | 8/1966 | O'Connor |
| 3,597,972 | A | 8/1971 | Ryder |
| 3,994,175 | A | 11/1976 | Yamaguchi et al. |
| 4,240,282 | A | 12/1980 | Nelson |
| 5,900,547 | A | 5/1999 | Bartkiewicz |
| 6,826,956 | B1 | 12/2004 | Mathews |
| 7,228,737 | B2 | 6/2007 | Summer et al. |
| 2010/0013112 | A1* | 1/2010 | Forkosh ................ 261/128 |

* cited by examiner

*Primary Examiner* — Harshad Patel
(74) *Attorney, Agent, or Firm* — Brooks Kushman P.C.

(57) ABSTRACT

An assembly for measuring both the level and specific gravity of a liquid in a container includes a first sensor arrangement for sensing the level of the liquid in the container, and a second sensor arrangement for sensing the specific gravity of the liquid. The first sensor arrangement measures and then independently outputs at least one signal relating to the liquid level in the container. The second sensor arrangement measures and then independently outputs at least one signal relating to the specific gravity of the liquid in the container, thereby providing an integrated device to measure both parameters of the liquid.

18 Claims, 2 Drawing Sheets

ASSEMBLY FOR MEASURING THE SPECIFIC GRAVITY AND LEVEL OF A LIQUID

CROSS-REFERENCE TO RELATED APPLICATIONS

This application claims the benefit of U.S. provisional application Ser. No. 60/839,872, filed Aug. 24, 2006 which is hereby incorporated by reference in its entirety.

BACKGROUND OF THE INVENTION

1. Field of the Invention

The present invention relates to an assembly for measuring the surface level and the specific gravity of a liquid.

2. Background Art

Many systems, both industrial and non-industrial, utilize liquid. For example, water, or liquids consisting primarily of water, are often used as a coolant. Acids, used for example in lead-acid batteries, and liquid desiccants, used in dehumidification or water collection systems, are also frequently used. Depending on the system, a knowledge of the characteristics of the liquid at some given time may be important.

In particular, it may be important to know what volume of liquid is available in a system. In the case of liquid residing in a container having a regular shape and a fixed volume, one way to determine the volume of liquid present is to measure the liquid level. Another important characteristic of the liquid may be its specific gravity, which could be indicative of the concentration of constituent materials making up the liquid.

Some systems for measuring the level and specific gravity of a liquid are only able to measure an increase or decrease in the specific gravity or liquid level as they relate to one another. In conventional systems, when there is a change in either the liquid level or specific gravity, the system detects and then outputs a single signal indicating such a change. These systems are unable to determine whether the detected change is attributable to a change in the liquid level or the specific gravity, and therefore, are of limited utility. They provide only general information, which may not be adequate in many applications. Such systems are only able to indicate that one or both of the liquid level and specific gravity have changed, without indicating which has occurred.

One system that combines measurement of liquid level and specific gravity is U.S. Pat. No. 3,994,175 ("the '175 patent"), entitled "Device for Detecting Specific Gravity and Liquid Level of a Liquid," issued on Nov. 30, 1976. The '175 patent describes a system where a voltage signal is created when the liquid level, the specific gravity, or a combination of the two, falls below a predetermined level. When this occurs, the signal triggers an alarm indicating that either one or both of these parameters has fallen below the critical level. Although the system described in the '175 patent is affected by both liquid level and specific gravity, it is unable to indicate a change in either of these values independently of the other.

Another limitation of conventional systems is that they may not operate in a corrosive environment. Measurement devices comprising metallic materials do not operate well, or at all, in corrosive environments, such as in desiccant in a water management system, or in acid in batteries. Finally, many conventional systems are expensive to manufacture. These systems generally require two separate devices to measure both the liquid level and the specific gravity of the liquid. This can be expensive, cumbersome and require an inefficient use of space. Therefore, it would be desirable to have a system that can independently measure and display readings of both the liquid level and the specific gravity of a liquid utilizing a single, integrated device. A need also exists for such a system that can operate well in a corrosive environment, and is cost effective to manufacture.

SUMMARY OF THE INVENTION

The present invention provides an assembly that measures both a level and specific gravity of a liquid in a container. The assembly includes a first sensor arrangement for sensing the surface level of the liquid, and a second sensor arrangement for measuring the specific gravity of the liquid. The first sensor arrangement includes at least one first sensor that senses and outputs, independently of other sensors, at least one signal related to the level of the liquid. The second sensor arrangement includes at least one second sensor that senses and outputs at least one signal related to the specific gravity of the liquid, and does so independently of the liquid level.

The first sensor arrangement further includes a first sleeve having the first sensors mounted thereon. The second sensor arrangement further includes a second sleeve having the second sensors mounted thereon. In at least one embodiment, the first and second sleeves, respectively, comprise a cylinder. At least one of the sleeves is configured to move relative to the other one of the sleeves to actuate the first or second sensors. The first sensor arrangement further includes the first sleeve, the second sleeve and a support configured to be fixed to a container. At least one of the first and second sleeves is configured to move relative to the other one of the sleeves to actuate the first sensors. In one embodiment, a float is mounted to the second sleeve, allowing it to move relative to the level of the liquid in the container. The movement of the second sleeve affects the internal communication of at least one of the first sensors to indicate the level of the liquid. The first and second sensors are mounted along a length of the first sleeve and second sleeve respectively, and may include at least one of the following: an optical sensor, an ultrasonic sensor or a capacitive sensor.

In embodiments where the first sensors are optical sensors, a light emitting diode communicates with a phototransistor by transmitting a light signal that is received by the phototransistor. When the second sleeve moves between the light emitting diode and the phototransistor, it prevents the light emitting diode from communicating with the phototransistor. The sensor then sends a signal to a controller indicating whether the signal was received by the phototransistor. In embodiments where the first sensors are ultrasonic sensors, the ultrasonic sensor is mounted to the first sleeve and sends a signal which reflects off of the second sleeve and returns to the sensor. The level of the liquid may then be determined by the sensor by measuring the amount of time it takes for the signal to return to the sensor. When the surface level of the liquid has reached a height which lifts the second sleeve to a height which obstructs the transmission of the ultrasonic signal, the ultrasonic signal will reflect off the second sleeve and return to the ultrasonic sensor in less time then it would take if the second sleeve were not obstructing the signal and the signal traveled to the opposite wall of the first sleeve and bounced back. This measurement is then transmitted to the controller. Finally, in embodiments where the first sensors are capacitive sensors, the level of the liquid is determined by measuring changes in capacitance between conducting plates which are mounted to the first sleeve. These capacitance measurements are then transmitted to the controller to identify the level of the liquid. The same principles may be applied in measuring the specific gravity of the liquid where a specific gravity gauge is used, as described below.

In at least one embodiment, the second sensor arrangement further includes a specific gravity gauge. At least one of the second sleeve and specific gravity gauge is configured to move relative to the other to actuate the second sensors. The specific gravity gauge has a fixed specific gravity, and is displaced in the liquid relative to the second sleeve based on the specific gravity of the liquid. This affects the internal communication of at least one of the second sensors to indicate the specific gravity of the liquid. The sensors described above are similarly used in the second sensor arrangement. In this arrangement, instead of taking measurements relative to the first and second sleeves, measurements are taken relative to the second sleeve and the specific gravity gauge.

In at least one embodiment, an assembly for measuring both a liquid's specific gravity and surface level in a container is provided. The assembly comprises a first member having a first sensor. A second member is associated with the first member. The second member is supported on a surface of the liquid and includes a second sensor. The second member is configured to move with respect to the first member as the surface level of the liquid changes. The second member affects the first sensor and thereby allows the first sensor to measure the level of the surface of the liquid when the second member is disposed at a predetermined level with respect to the first member. A third member is associated with the second member. The third member is supported by the liquid and is configured to move with respect to the second member as the specific gravity of the liquid changes. The third member affects the second sensor and thereby allows the second sensor to measure the specific gravity of the liquid when the third member is disposed at a predetermined level with respect to the second member.

In at least one embodiment, a system for managing water content in a fluid is provided. The system comprises a first container having an inlet to receive the fluid and an outlet to exhaust the fluid. A liquid desiccant may be disposed within the first container. A first subsystem for cooling the liquid desiccant may also be included. A second subsystem for circulating the liquid desiccant through the container may be provided such that the liquid desiccant contacts and extracts water from the fluid. The system also includes an assembly for independently measuring a specific gravity and a surface level of the liquid desiccant in the container. The assembly includes a first member having a first sensor. A second member is associated with the first member. The second member is supported on a surface of the liquid desiccant and has a second sensor. The second member is configured to move with respect to the first member as the surface level of the liquid desiccant changes. The second member affects the first sensor when the second member is disposed at a predetermined level with respect to the first member. A third member is associated with the second member. The third member is supported by the liquid desiccant and may be configured to move with respect to the second member as the specific gravity of the liquid desiccant changes. The third member affects the second sensor when the third member is disposed at a predetermined level with respect to the second member.

Embodiments of the present invention provide advantages over conventional liquid level and specific gravity sensors. The level and specific gravity of the liquid may be independently measured in an integrated device. Further, embodiments of the present invention allow for better functionality in a corrosive environment, such as in a desiccant in a water management system or in a battery, because the device may be constructed almost entirely of plastic. Finally, the embodiments of the present invention may provide a manufacturing cost savings.

DETAILED DESCRIPTION OF THE PREFERRED EMBODIMENT(S)

Figure 1:
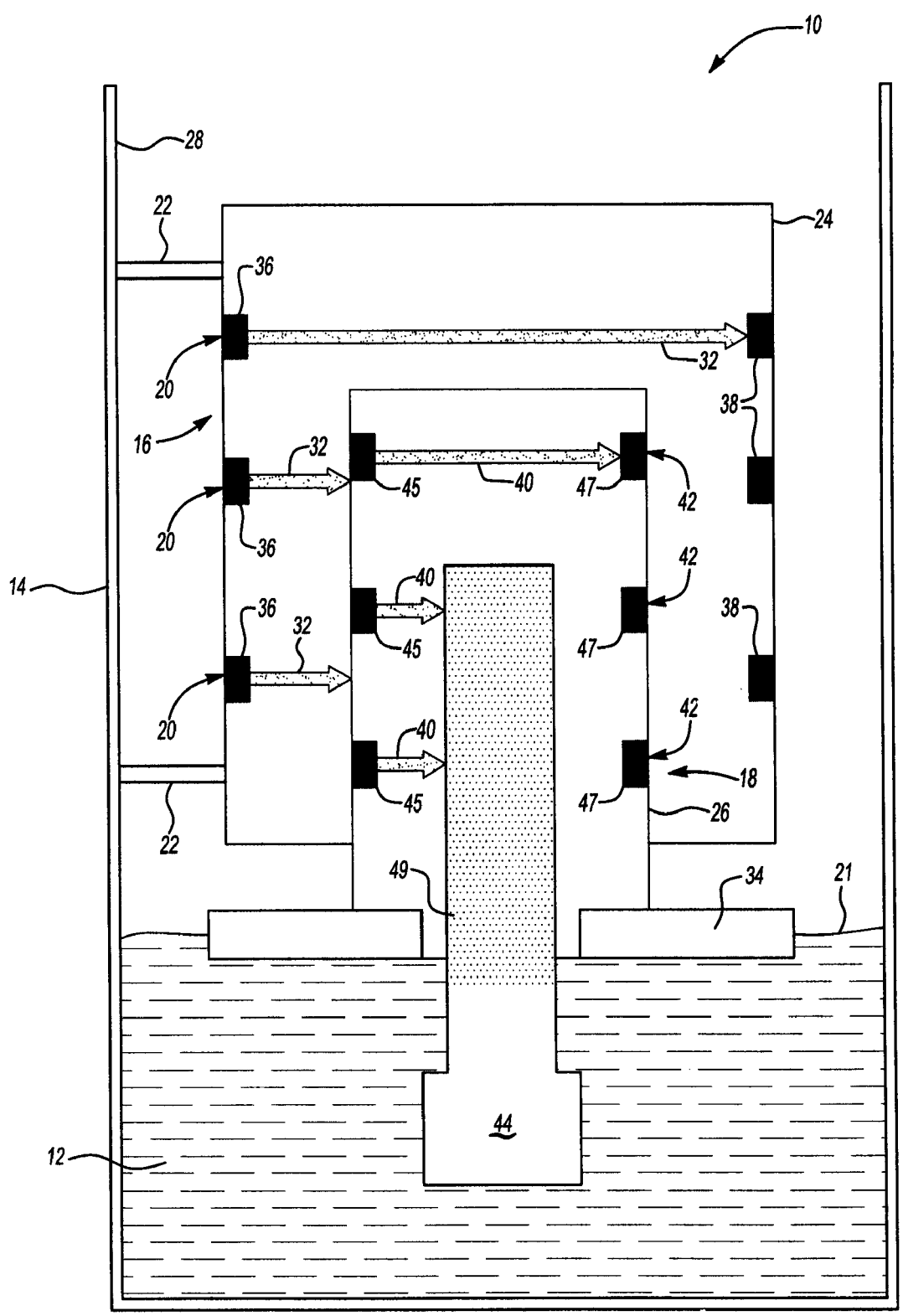
FIG. 1 is a schematic view illustrating an embodiment of an assembly for measuring a surface level and a specific gravity of a liquid in a container in accordance with the present invention.

FIG. 1 shows a measurement assembly 10 for measuring a level and specific gravity of a liquid 12 in a container 14 in accordance with one embodiment of the present invention. The measurement assembly 10 includes first and second sensor arrangements 16, 18, which, as explained more fully below, are made up of a number of components. The first sensor arrangement 16, which measures the surface 21 of liquid 12 in container 14, includes first sensors 20, supports 22, a first sleeve 24 and a second sleeve 26. The first and second sleeves, shown in a side view in FIG. 1, are generally cylindrical in this embodiment, and have longitudinal axes. In other embodiments, the first and second sleeves may have other shapes and configurations. The first sensors 20 are mounted along an internal length of the first sleeve 24, and are configured to independently send respective first signals 32 to measure the level of the liquid 12 in the container 14. The level measured is then sent to a controller (not shown) which may be used to control the level of the liquid 12 in the container 14. In the embodiment shown in FIG. 1, the supports 22 are fixed to an internal wall 28 of the container 14. The supports 22 are also fixed along a length of the second sleeve 26, and maintain a distance between the internal wall 28 and the first sleeve 24. Although the illustration in FIG. 1 includes two supports 22, it is understood that the placement, number and size of the supports 22 may differ in different embodiments.

The second sleeve 26, which typically has a diameter less than the diameter of the first sleeve 24, is located within the first sleeve 24. Although not fixed to the first sleeve 24, the second sleeve 26 is aligned so that it may move up and down within the first sleeve 24 as the liquid level in the container 14 increases or decreases. A float 34 is mounted to the second sleeve 26. As the liquid level increases and decreases, the float 34 moves up and down relative to the surface of the liquid 12. Accordingly, since the float 34 is attached to the second sleeve 26, the second sleeve 26 also moves according to the level of the liquid 12.

When the second sleeve 26 moves up and down, it affects the internal communication of at least one of the first sensors 20. In the embodiment shown in FIG. 1, the first sensors 20 are optical sensors, each of which includes a light emitting diode (LED) 36 that is positioned across from a corresponding phototransistor 38. As the second sleeve 26 moves up and down according to the level of the liquid 12, the second sleeve 26 impedes or allows communication between one of the light emitting diodes 36 and its respective phototransistor 38. When the second sleeve 26 is positioned between the light emitting diode 36 and the phototransistor 38, the communication is interrupted, thereby affecting the first signal 32. When there is more than one first sensor 20 located along a length of the first sleeve 24, it is possible to measure different liquid levels of the liquid 12. In embodiments where there is only one first sensor 20, it is only possible to measure a single level, which may be all that is required in some applications. Although optical sensors are described above as being attached to the first sleeve 24, other types of sensors may also be used. Such other examples include ultrasonic sensors and capacitive sensors. The movement of the floating sleeve 26 actuates each of the different types of sensors. The precision of the liquid level measurement depends at least in part on the number of sensors placed along the length of the first sleeve 24.

In embodiments where the first sensors 20 are ultrasonic sensors, the ultrasonic sensor, mounted to the first sleeve 24, sends a signal which reflects off of the second sleeve 26 and returns to the first sensor 20. Because ultrasonic sensors would use the second sleeve 26 as a reflector, they may be mounted on only one side of the first sleeve 24, like the LED's 36 without their corresponding phototransistors 38. The level of the liquid may then be measured by the first sensor 20 by measuring the amount of time it takes for the signal to return to the first sensor 20. This measurement is then transmitted to a controller to determine the level of the liquid. In embodiments where the first sensors 20 are capacitive sensors, the level of the liquid is determined by measuring changes in capacitance between conducting plates which are mounted to the first sleeve 24, and which may be positioned like the LED's 36 and their corresponding phototransistors 38. These capacitance measurements would then be transmitted to the controller to determine the level of the liquid. The same principles may be applied in measuring the specific gravity of the liquid.

FIG. 1 also shows the second sensor arrangement 18, which includes second sensors 42, second sleeve 26, and a specific gravity gauge 44. The second sensors 42 transmit respective second signals 40 to determine the specific gravity of the liquid 12. The second sensors 42 are mounted along an internal length of the second sleeve 26. The specific gravity gauge 44, which has a diameter less than the diameter of the second sleeve 26, is positioned within the second sleeve 26. Specific gravity gauge 44 is able to move freely as the specific gravity and level of the liquid 12 increases and decreases.

The second sleeve 26, with float 34 attached, moves up and down as the level of the liquid 12 increases and decreases. Accordingly, unlike the first sensors 20 in the first sensor arrangement 16, which are attached to a fixed first sleeve 24, the second sensors 42 move with the second sleeve 26 as the liquid level increases or decreases. In the embodiment shown in FIG. 1, the second sensors 42 are optical sensors, each having a light emitting diode 45 positioned across from a phototransistor 47. As the specific gravity of the liquid 12 in the container 14 increases and decreases, the specific gravity gauge 44 moves accordingly. As the specific gravity of the liquid 12 increases, the specific gravity gauge 44 will rise, thereby impeding communication of at least one of the second sensors 42. Conversely, as the specific gravity of the liquid 12 decreases, the specific gravity gauge 44 will fall, thereby allowing communication between at least some of the light emitting diodes 45 and their respective phototransistor 47. Although optical sensors are described above as being fixed on the second sleeve 26, other types of sensors may also be used. Such other examples include ultrasonic sensors capacitive sensors. These alternative sensors operate in the same manner described above for measuring the level of the liquid except the communication here is between the second sleeve 26 and the specific gravity gauge 44.

When there is more than one second sensor 42 located along a length of the second sleeve 26, it is possible to measure the specific gravity of the liquid 12 at different specific gravity values. When there is only one second sensor 42, it is only possible to measure whether the specific gravity is above or below the level of the single second sensor 42. The precision of the specific gravity measurement depends at least in part on the number of sensors placed along the length of the second sleeve 26.

Much of the structure of the measurement assembly 10 may be made using lightweight, inexpensive material such as plastic. The supports 22, the first sleeve 24, the second sleeve 26 and the float 34 may all be constructed using plastic. While plastic is the preferred material for construction of these elements, they are not exclusive in nature. Other materials suitable for use in the production of these elements include, but are not limited to, stainless steel and aluminum. Additionally, the specific gravity gauge 44 may be made of glass, although it may also be made of any other suitable material or materials. In embodiments where the specific gravity gauge 44 is made of transparent materials, at least a portion of it may be made opaque by using a marker or other suitable means—see, for example, the opaque portion 49 on the specific gravity gauge 44. Such opacity may be required when using optical sensors.

Figure 2:
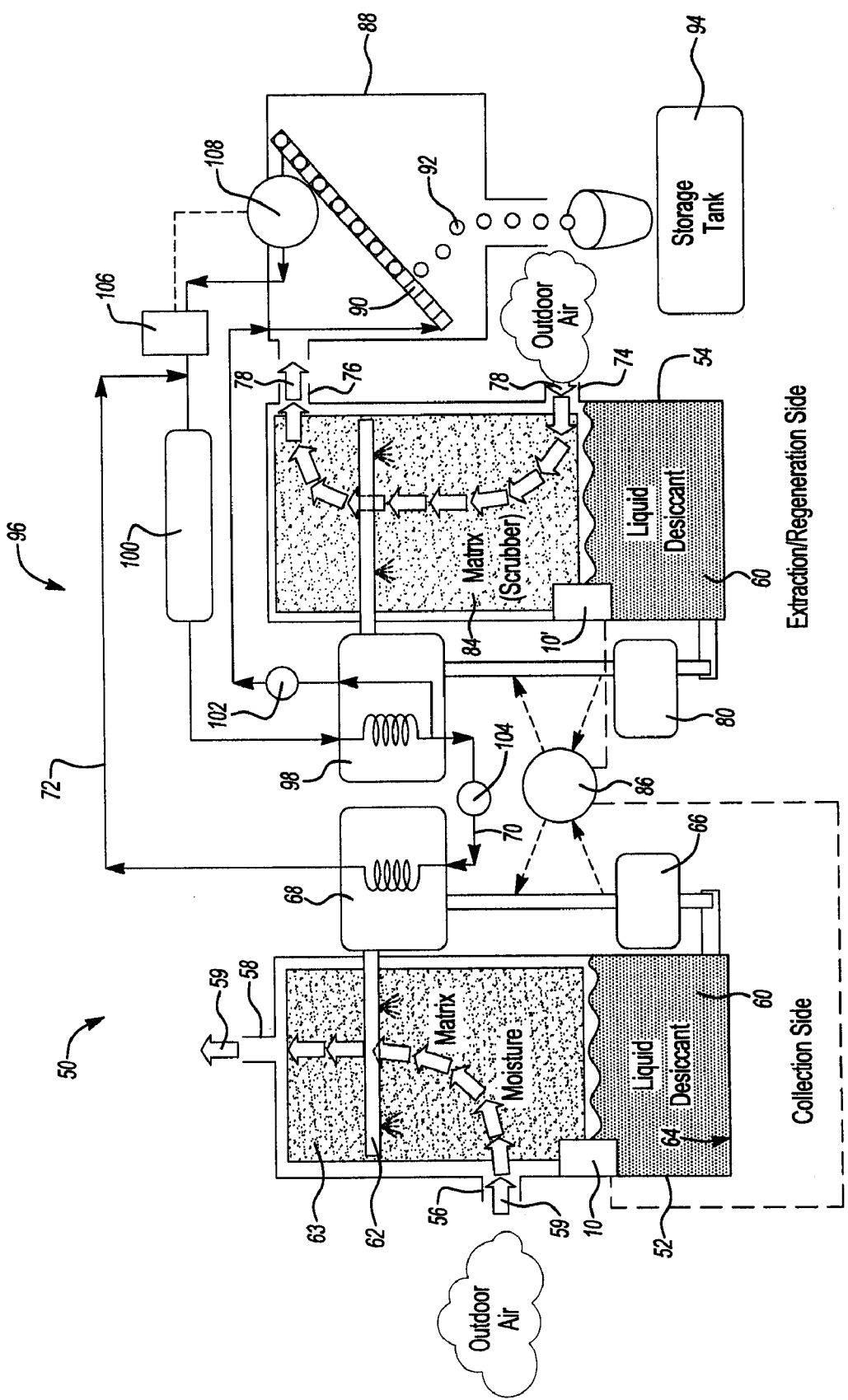
FIG. 2 is a schematic view illustrating a system for managing water content in a liquid including subsystems for water collection and water extraction, the system utilizing the measuring assembly shown in FIG. 1.

FIG. 2 shows the measurement assembly 10 used with a system 50 for managing water content in a fluid. In particular, the system 50 is configured to manage the water content in air—either to collect water from the air for storage and subsequent use, or to control the humidity of the air. Although the examples presented herein utilize ambient air as the fluid whose water content is being managed, the system 50 is capable of managing the water content of other fluids as well. The system 50 includes a first chamber, or collection chamber 52, and a second chamber, or regeneration chamber 54. The collection chamber 52 includes an inlet 56 and an outlet 58 which allow a first airflow 59 to flow through the collection chamber 52. As the air flows through the collection chamber 52, it contacts a desiccant 60, which, in the embodiment shown in FIG. 2, is sprayed into the chamber 52 via a conduit 62.

As the air moves through the collection chamber 52, vaporized water is condensed out, and collects with the desiccant 60 in a collection chamber sump 64 in the bottom portion of the chamber 52. The desiccant 60 is diluted as it adsorbs or absorbs the water from the air. Although the desiccant 60 shown in FIG. 2 is all liquid, the system 50 contemplates the use of dual phase desiccants—e.g., solid and liquid. The measuring device 10 is used to measure the level and specific gravity of the desiccants in both the collection chamber 52 and the regeneration chamber 54.

Inside the collection chamber 52 is a matrix material 63. The matrix 63 can be a sponge or other medium or media effective to facilitate contact between the desiccant 60 and the air flowing through the collection chamber 52. The desiccant 60 is pumped into the conduit 62 by a pump 66. The pump 66 pumps the desiccant 60 through a first heat exchanger 68 prior to its introduction into the collection chamber 52. By cooling the desiccant 60, its ability to remove water from the first airflow 59 is increased. A fluid, such as a refrigerant, is passed through the first heat exchanger 68 via conduits 70, 72. The desiccant 60 is cooled in the first heat exchanger 68 to a temperature below that of the first airflow 59. In this way, the airflow 59 is cooled as it passes through the collection chamber 52.

The regeneration chamber 54 also includes an inlet 74 and an outlet 76, which facilitate movement of a second airflow 78 into and out of the regeneration chamber 54. As with the collection chamber 52, the regeneration chamber 54 also includes a pump 80 which is used to pump the desiccant 60 into the regeneration chamber 54 through a conduit 72. The desiccant 60 is sprayed into the regeneration chamber 54 to contact a matrix 84, which, like the matrix 63, may be a sponge or other medium or media.

Between the two chambers 52, 54 is a flow controller 86 in communication with the measurement assembly 10 and which can include an electronic valve, operable to allow the hydrous desiccant from the collection chamber 52 to mix with desiccant 60 in the regeneration chamber 54, and vice versa. When the desiccant 60 in the collection chamber 52 absorbs water from the air, the liquid level of the desiccant 60 increases while the specific gravity of the desiccant decreases. As the concentration of water in the desiccant 60 increases, the desiccant 60 is less able to absorb additional water. In order to maintain desiccant 60 in the collection chamber which is optimally able to absorb water, the measurement assembly 10 is mounted to the collection chamber 52 to monitor the liquid level and specific gravity of the desiccant. When the liquid level increases above a desired level or when the specific gravity of the desiccant 60 decreases below a desired value, the flow controller 86 may be opened, and some more concentrated desiccant from the regeneration chamber 54 is exchanged with desiccant from the collection chamber 52. As a result, the desiccant in the collection chamber 52 is more easily able to absorb water from the moist air, and the desiccant in the regeneration chamber 54 is more easily able to release water from the desiccant which may be used for drinking or other uses.

The warm, humid air 78 leaving the regeneration chamber 54 can be introduced into a system heat exchanger, or evaporator 88. The evaporator 88 includes a contact surface 90, which causes water 92 to condense out of the humid air stream 78. The water 92 may be collected in a storage tank 94 for later use.

The evaporator 88 is part of a refrigeration subsystem 96, which includes the first heat exchanger 68 and a second heat exchanger 98. The first and second heat exchangers 68, 98 respectively act as an evaporator and condenser within the refrigeration subsystem 96. A refrigerant is pumped through the refrigeration subsystem 96 by a compressor 100, while throttling devices 102, 104 facilitate expansion of the refrigerant before it reaches a respective evaporator 68, 88.

To selectively control the flow of the refrigerant through the evaporators 68, 88, a control valve 106 is used. The control valve 106 is in communication with a sensor 108 at least partly disposed within the evaporator 88. The sensor 108 is configured to sense a parameter of the second airflow 78 after it has picked up water in the regeneration chamber 54. For example, the sensor 108 can be a hygrometer or other device capable of measuring the humidity of the airflow 78, which may be convenient when the system 50 is used as a dehumidifier. Alternatively, the sensor 108 can be a temperature sensor configured to sense a temperature of the airflow 78, which may be convenient when the system 50 is used to produce water. In any case, the sensor 108 can output signals related to the sensed parameter to control the valve 106.

As shown in FIG. 2, the sensor 108 is configured to sense the temperature of the airflow 78 in the evaporator 88. When the valve 106 is open, thereby allowing refrigerant to flow through the evaporator 88, the evaporator 88 cools the airflow 78. The sensor 108 is configured such that when the sensed temperature drops to a predetermined set point the sensor 108 signals the valve 106 to close. This stops the refrigerant from flowing through the evaporator 88, and increases the amount of refrigerant flowing through the other evaporator, or first heat exchanger 68. In this way, the heat absorbing capacity of the evaporator 88 is reduced, while the heat absorbing capacity of the evaporator 68 is increased. The increased cooling of the desiccant 60 entering the collection chamber 52 results in more water being absorbed from the first airflow 59, and thereby increases the vapor pressure of the desiccant 60.

As an alternative to, or in conjunction with, the measurement assembly 10 disposed in the collection chamber 52, a second measurement assembly 10' may be mounted in the regeneration chamber 54 to monitor its desiccant level and specific gravity. As shown in FIG. 2, the measurement assembly 10' is also in communication with the flow controller 86. In this scenario, if the desiccant liquid level decreases below a threshold point, or the specific gravity increases above a desired value, the flow controller 86 may be opened so that desiccant 60 in the regeneration chamber 54, having a lower water content, may switch tanks with the desiccant 60 in the collection chamber 52, with a higher water content. In this way, the desiccant in the collection chamber 52 may once again more easily absorb water, while the saturated desiccant 60 in the regeneration chamber 54 may more easily release water into the airflow 78.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An assembly for independently measuring both a liquid's specific gravity and surface level in a container, the assembly comprising:
   a first member having a first sensor;
   a second member associated with the first member, the second member being supported on a surface of the liquid and having a second sensor, the second member being configured to move with respect to the first member as the surface level of the liquid changes, the second member affecting the first sensor when the second member is disposed at a predetermined level with respect to the first member; and
   a third member associated with the second member, the third member being supported by the liquid and configured to move with respect to the second member as the specific gravity of the liquid changes, the third member affecting the second sensor when the third member is disposed at a predetermined level with respect to the second member.

2. The assembly of claim 1 wherein the first member is configured to receive the second member and the second member is configured to slide with respect to the first member.

3. The assembly of claim 2 wherein the second member is configured to receive the third member and the third member is configured to slide with respect to the second member.

4. The assembly of claim 3 wherein the first member and the second member each comprise a respective sleeve.

5. The assembly of claim 1 wherein the first member includes a plurality of the first sensors, each of the first sensors being disposed at a different position along a length of the first member.

6. The assembly of claim 1 wherein the second member includes a plurality of the second sensors, each of the second sensors being disposed at a different position along a length of the second member.

7. The assembly of claim 6 wherein the first member includes a plurality of the first sensors, each of the first sensors being disposed at a different position along a length of the first member.

8. The assembly of claim 1 wherein the second member includes a floatation device.

9. The assembly of claim 1 wherein the third member is partially disposed within the liquid and partially disposed above the surface of the liquid.

10. The assembly of claim 1 wherein the third member has a substantially constant specific gravity such that the third member's vertical position in the fluid is determined by the fluid's specific gravity and changes in the third member's vertical position correspond with changes in the liquid's specific gravity.

11. The assembly of claim 1 wherein the first sensor is at least one of an optical sensor, an ultrasonic sensor, a capacitive sensor or a floating electrode sensor.

12. The assembly of claim 1 wherein the second sensor is at least one of an optical sensor, an ultrasonic sensor, a capacitive sensor or a floating electrode sensor.

13. The assembly of claim 1 wherein the first member is mounted to the container and is substantially stationary therewith.

14. A system for managing water content in a fluid, the system comprising:
a first container having an inlet to receive a fluid and an outlet to exhaust the fluid;
a liquid desiccant disposed within the first container;
a first subsystem for cooling the liquid desiccant;
a second subsystem for circulating the liquid desiccant through the container such that the liquid desiccant contacts and extracts water from the fluid; and
an assembly for independently measuring a specific gravity and a surface level of the liquid desiccant in the container, the assembly having:
a first member having a first sensor;
a second member associated with the first member, the second member being supported on a surface of the liquid desiccant and having a second sensor, the second member being configured to move with respect to the first member as the surface level of the liquid desiccant changes, the second member affecting the first sensor when the second member is disposed at a predetermined level with respect to the first member; and
a third member associated with the second member, the third member being supported by the liquid desiccant and configured to move with respect to the second member as the specific gravity of the liquid desiccant changes, the third member affecting the second sensor when the third member is disposed at a predetermined level with respect to the second member.

15. The system of claim 14 further comprising:
a second container in fluid communication with the first container, the second container having an inlet to receive a fluid and an outlet to exhaust the fluid;
a liquid desiccant disposed within the second container;
a third subsystem for circulating the liquid desiccant through the second container such that the fluid contacts and extracts water from the liquid desiccant;
a controller in communication with the assembly, the controller controlling the flow of liquid desiccant between the first container and the second container based on the liquid desiccant's sensed surface level and the liquid desiccant's sensed specific gravity; and
an evaporator for extracting water out of the fluid after the fluid has contacted the liquid desiccant and has been exhausted from the second container.

16. The system of claim 14 wherein the first member is disposed within the container, the second member is configured to move vertically with respect to the first member, and the third member is configured to move vertically with respect to the second member.

17. The system of claim 16 wherein the first member includes a sleeve configured to receive the second member and the second member includes a sleeve configured to receive the third member.

18. The system of claim 17 wherein the first member includes a plurality of the first sensors spaced apart along a longitudinal axis of the first member and the second member includes a plurality of the second sensors spaced apart along the longitudinal axis of the second member, the first member being configured to determine the surface level of the liquid by detecting which of the first sensors are affected by the second member and the second member being configured to determine the specific gravity of the liquid by detecting which of the second sensors are affected by the third member.

* * * * *